US012648846B2

(12) United States Patent
Maiorano

(10) Patent No.: US 12,648,846 B2
(45) Date of Patent: Jun. 9, 2026

(54) TRANSCATHETER VALVE HAVING REDUCED SEAM EXPOSURE

(71) Applicant: MEDTRONIC, INC., Minneapolis, MN (US)

(72) Inventor: Alaena DeStefano Maiorano, Huntington Beach, CA (US)

(73) Assignee: Medtronic, Inc., Minneapolis, MN (US)

( * ) Notice: Subject to any disclaimer, the term of this patent is extended or adjusted under 35 U.S.C. 154(b) by 1057 days.

(21) Appl. No.: 17/677,696

(22) Filed: Feb. 22, 2022

(65) Prior Publication Data

US 2022/0175519 A1 Jun. 9, 2022

Related U.S. Application Data

(60) Division of application No. 16/419,749, filed on May 22, 2019, now Pat. No. 11,284,995, which is a continuation of application No. 15/282,023, filed on Sep. 30, 2016, now Pat. No. 10,327,893, which is a division of application No. 13/310,949, filed on Dec. 5, 2011, now Pat. No. 9,480,558.

(51) Int. Cl.
*A61F 2/24* (2006.01)

(52) U.S. Cl.
CPC .......... *A61F 2/2415* (2013.01); *A61F 2/2412* (2013.01); *A61F 2/2418* (2013.01); *A61F 2220/0075* (2013.01)

(58) Field of Classification Search
CPC ........ A61F 2/24; A61F 2/2418; A61F 2/2415; A61F 2250/0069; A61F 2/2463; A61F 2/246; A61F 2/2427; A61F 2/2466
See application file for complete search history.

(56) References Cited

U.S. PATENT DOCUMENTS

| | | | |
|---|---|---|---|
| 5,855,597 A | 1/1999 | Jayaraman | |
| 5,935,163 A | 8/1999 | Gabbay | |
| 7,914,569 B2 | 3/2011 | Nguyen et al. | |
| 9,480,558 B2 | 11/2016 | Destefano | |
| 11,896,481 B2 * | 2/2024 | Bruchman | A61F 2/2412 |
| 12,004,947 B1 * | 6/2024 | Corona | A61F 2/2415 |
| 12,115,063 B2 * | 10/2024 | Bruchman | A61F 2/2418 |
| 12,226,311 B2 * | 2/2025 | Chung | A61F 2/2409 |
| 12,295,833 B2 * | 5/2025 | Levi | A61F 2/2418 |
| 2003/0114913 A1 | 6/2003 | Spenser et al. | |
| 2005/0137688 A1 | 6/2005 | Salahieh et al. | |
| 2006/0259136 A1 * | 11/2006 | Nguyen | A61F 2/2412 |
| | | | 623/2.18 |
| 2006/0276813 A1 | 12/2006 | Greenberg | |

(Continued)

FOREIGN PATENT DOCUMENTS

| | | |
|---|---|---|
| EP | 2520249 | 11/2012 |
| EP | 2787924 | 9/2017 |
| WO | 9829057 | 7/1998 |

(Continued)

*Primary Examiner* — Seema Mathew
(74) *Attorney, Agent, or Firm* — Medler Ferro Woodhouse & Mills PLLC

(57) ABSTRACT

A transcatheter valve having an expandable frame and a collapsible multi-portion skirt within the frame are provided with seams between the portions of the skirt that are located to cooperate with features of the frame and thereby reduce the exposure of the seams.

33 Claims, 6 Drawing Sheets

(56)               References Cited

U.S. PATENT DOCUMENTS

2010/0082094  A1      4/2010   Quadri et al.
2025/0255716  A1*    8/2025   Kelly  ................... A61F 2/2418

FOREIGN PATENT DOCUMENTS

| WO | 200149213 | 7/2001 |
| WO | 2006127765 | 11/2006 |
| WO | 2009053497 | 4/2009 |
| WO | 2009149462 | 12/2009 |
| WO | 2010006627 | 1/2010 |
| WO | 2011079803 | 7/2011 |
| WO | 2011147849 | 12/2011 |
| WO | 2012032187 | 3/2012 |
| WO | 2012039753 | 3/2012 |
| WO | 2013085719 | 6/2013 |

* cited by examiner

TRANSCATHETER VALVE HAVING REDUCED SEAM EXPOSURE

RELATED APPLICATIONS

This application is a Division of U.S. patent application Ser. No. 16/419,749, filed May 22, 2019, which is a Division of U.S. patent application Ser. No. 15/282,023, filed Sep. 30, 2016, and U.S. patent application Ser. No. 13/310,949, filed Dec. 5, 2011, the disclosures of all are herein incorporated by reference in their entirety.

TECHNICAL FIELD

This invention relates to transcatheter valves, such as heart valves, which have an expandable frame and a collapsible multi-portion skirt within the frame. Such assemblies are suitable for percutaneous transluminal delivery to replace a diseased aortic valve in patients suffering from cardiac valve dysfunction, such as aortic valve regurgitation or aortic stenosis.

BACKGROUND

Recently developed transcatheter valves conform to a patient's anatomy while providing a uniform degree of rigidity and protection for critical valve components. They are capable of deforming circumferentially to adapt to the shape of the pre-existing valve annulus, but are not susceptible to deformation or migration due to normal movement of the heart. In one type of design, the valve prosthesis has a multi-level component that is anatomically shaped when deployed, thereby enhancing anchoring of the valve and reducing the risk of migration and paravalvular leaks. A particularly successful assembly of this type is disclosed in U.S. Pat. No. 7,914,569, the entire contents of which is incorporated by reference.

SUMMARY

It has been discovered that the assembly of the type is disclosed in U.S. Pat. No. 7,914,569 may be improved by using differently formed components for the valve skirt, such that improved performance may be achieved without any departure from the successful design disclosed in that patent. Specifically, it has been discovered that the profile (diameter) of the assembly prior to deployment may be reduced by rearranging certain aspects of the assembly to reduce the bulk of the assembly and exploit the structure of the frame portion of the assembly to maintain the reduced bulk after deployment.

To accomplish these advantages, an improved valve prosthesis comprises a self-expanding frame having a longitudinal axis and an inflow end, and comprising a plurality of cells; a valve body having a skirt with a bottom edge sewn to the inflow end of the frame, a plurality of leaflets sewn to the skirt along a seam having upper and lower halves, a lower apex region, and at least one side seam between a point on the lower half of the seam (most preferably, the lower apex itself) and the bottom edge. The side seam may be substantially parallel to the longitudinal axis or it may make an acute angle with the longitudinal axis.

Regardless of angle, the skirt preferably has three substantially identical portions, with each portion being asymmetric about an axis substantially aligned with the longitudinal direction. However, in less preferred embodiments, non-identical portions are possible.

Or, alternatively, the skirt may have three substantially identical portions, the bottom edge of each portion having five end tabs symmetrically arranged about an axis of the skirt which is substantially aligned with the longitudinal direction and passes through an upper apex of the portion. In this case, the side seam extends between the lower apex region and an end tab which does not lie on the axis of the skirt.

Another variation has the skirt aligned with the frame such that the side seam substantially follows a line defined by three immediately adjacent nodes.

In any of the variations described above, it is preferred that the skirt be aligned with the frame such that the side seam and a line defined by three immediately adjacent nodes are aligned with each other within ±1 mm.

This summary of the claims has been presented here simply to point out some of the ways that the claims overcomes difficulties presented in the prior art, and to distinguish the claims from the prior art, but it is not intended to operate in any manner as a limitation on the interpretation of claims that are presented initially in the patent application and that are ultimately granted.

BRIEF DESCRIPTION OF THE DRAWINGS

These and other advantages and features will be more readily understood from the following detailed description of various preferred embodiments, when considered in conjunction with the drawings, in which like reference numerals indicate identical structures throughout the several views, and in which.

DETAILED DESCRIPTION

Figure 1:
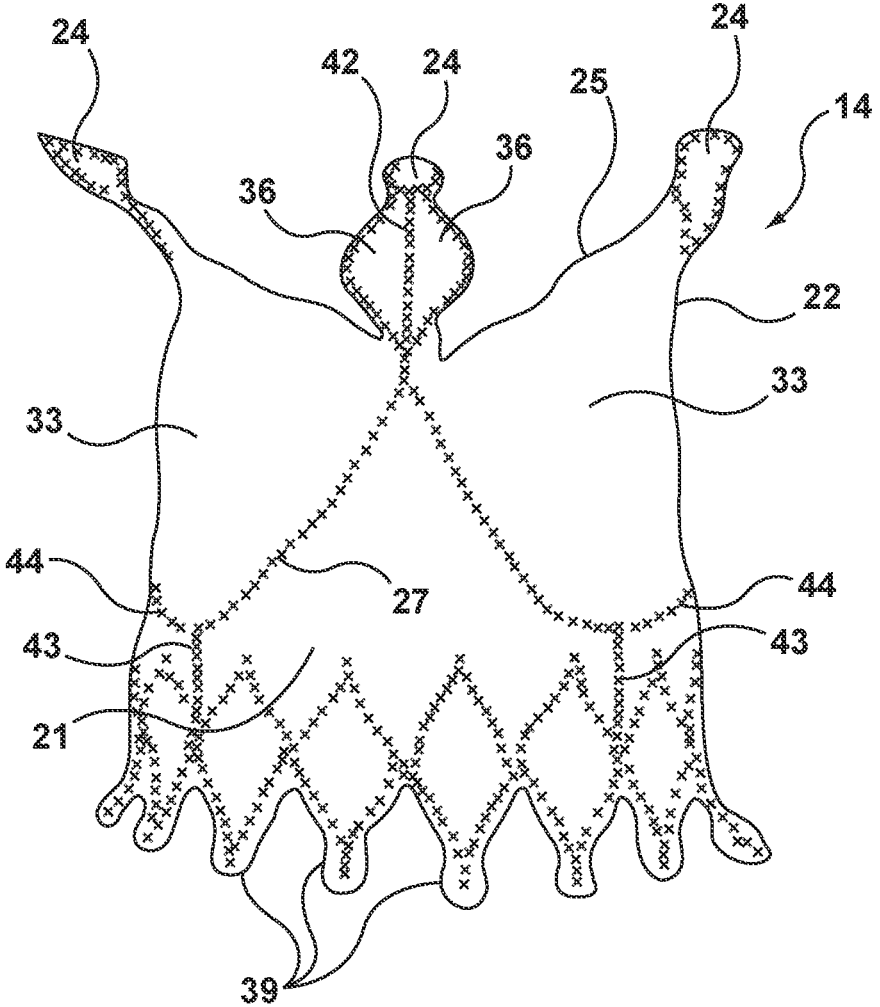
FIG. 1 is a side view of a fully assembled valve body with the surrounding frame omitted for clarity.

In the following detailed description, references are made to illustrative embodiments of methods and apparatus for carrying out the claims. It is understood that other embodiments can be utilized without departing from the scope of the claims.

By way of background, the currently successful transcatheter aortic valve prosthesis known by the tradename CoreValve® (Medtronic, Inc.) has a self-expanding multi-level frame which supports a valve body comprising a skirt and plurality of coapting leaflets. The frame has a contracted delivery configuration, in which the prosthesis may be stored within a catheter for percutaneous delivery, and an expanded deployed configuration having an asymmetric hourglass shape. The valve body skirt and leaflets preferably are constructed of porcine, bovine, equine or other mammalian tissue, such as pericardial tissue, and are sewn, welded, molded or glued together so as to efficiently distribute forces along the leaflets and to the frame. Alternatively, the valve body may comprise a synthetic or polymeric material. The frame comprises multiple levels, including a proximal conical inflow section, a constriction region and a flared distal outflow section. Each of the inflow and outflow sections is capable of deforming to a non-circular cross-section to conform to the patient's anatomy, while the constriction region is configured to retain a circular cross-section that preserves proper functioning of the valve body. The frame comprises a plurality of cells having a pattern that varies along the length of the frame to provide a high degree of anchoring and alignment of the valve prosthesis. The cell pattern further is selected to provide a uniform diameter where the commissural joints of the leaflets are attached to the frame, while permitting the inflow and outflow regions to expand to conform to the patient's anatomy. In this manner, optimal functioning of the valve body may be obtained even though the frame may be deployed in anatomies having a range of sizes. In addition, the frame resists deformation caused by movement of the heart and enables a functional portion of the valve body to be disposed supra-annularly to the native valve, with a portion of the valve prosthesis extending into the native valve annulus. For aortic valve replacement, the valve body comprises a skirt coupled to three leaflets. Each of the components preferably is formed of animal pericardial tissue or synthetic material, and then sewn, glued, welded or molded together. The lateral ends of the leaflets include enlarged regions that are folded to both form the commissural joints and fasten the commissural joints to the frame. The skirt and leaflets further are configured so that the joints align with contours of the cell pattern of the frame. In a preferred embodiment, the commissural joints are affixed to the frame at locations above the area of coaptation, to provide a selectable center of coaptation of the leaflets. This design provides a more efficient delivery configuration because the commissures are not compressed against the leaflets when the valve prosthesis is reduced to the contracted delivery configuration. Additionally, by lengthening the distance to the commissures, the design mimics the functioning of natural tissue valves by distributing forces along the coaptation edges and reducing horizontal forces transmitted to the commissural joints.

In general terms, the valve prosthesis includes a self-expanding frame which supports a valve body and has a tri-level asymmetric hourglass shape with a conical proximal section, an enlarged distal section and a constriction region having a predefined curvature when the frame is deployed. The proximal section constitutes the "inflow" portion of the valve prosthesis and is disposed in the aortic annulus of the patient's left ventricle, while the distal section constitutes the "outflow" portion of the valve prosthesis and is positioned in the patient's ascending aorta. In a preferred embodiment the valve body comprises three leaflets that are fastened together at enlarged lateral end regions to form commissural joints, with the unattached edges forming the coaptation edges of the valve. The leaflets are fastened to a skirt, which is in turn affixed to the frame. The enlarged lateral end regions of the leaflets permit the material to be folded over to enhance durability of the valve and reduce stress concentration points that could lead to fatigue or tearing of the leaflets. The commissural joints are mounted above the plane of the coaptation edges of the valve body to minimize the contracted delivery profile of the valve prosthesis, while the configuration of the edges permits uniform stress distribution along the coaptation edges.

The frame preferably comprises a self-expanding structure formed by laser cutting or etching a metal alloy tube comprising, for example, stainless steel or a shape memory material such as nickel titanium. The frame has an expanded deployed configuration which is impressed upon the metal alloy tube using conventional techniques.

Referring now to FIG. 1, the valve prosthesis of this application continues the successful features of the prosthesis described above but improves upon it. In more specific terms, the valve prosthesis comprises valve body 14. Valve body 14 includes skirt 21, and leaflets 22. Leaflets 22 are attached along their bases to skirt 21, for example, using sutures or a suitable biocompatible adhesive. Adjoining pairs of leaflets are attached to one another at their lateral ends to form commissures 24, with free edges 25 of the leaflets forming coaptation edges that meet in an area of coaptation, as described more fully in U.S. Pat. No. 7,914, 569, the entire contents of which are incorporated by reference.

The curve formed at joint 27 between the base of each leaflet 22 and skirt 21 follows the contour of the cell pattern of the frame (not shown in FIG. 1), so that most of the length of joint 27 is directly supported by the frame, thereby transmitting forces applied to the valve body directly to the frame.

Skirt 21 and leaflet 22, in preferred embodiments, may be cut from a sheet of animal pericardial tissue, such as porcine pericardial tissue, although synthetic or polymeric material may be used. Cutting may be done either manually or using a die or laser cutting system. The pericardial tissue may be processed in accordance with conventional techniques for processing, forming and treating tissue valve material. Alternatively, skirt 21 and leaflet 22 may be constructed on a synthetic or polymeric material. In a preferred embodiment, skirt 21 and leaflets 22 have a thickness of between 0.004 inch and 0.016 inch. The thicknesses of skirt 21 and leaflets 22 may or may not be equal to each other.

Figure 2:
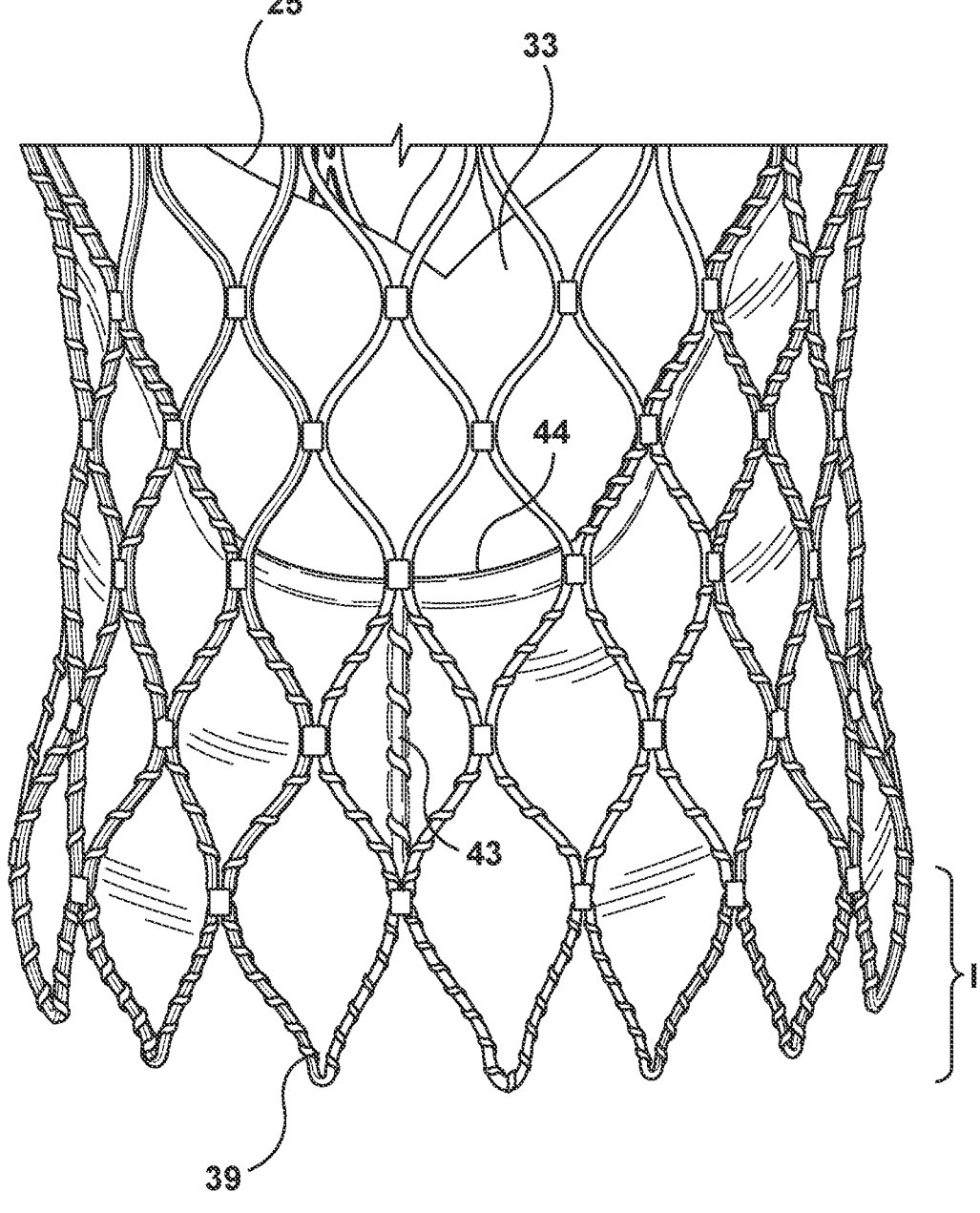
FIG. 2 is a close-up side view of the inflow end of a fully assembled valve body, including the surrounding frame, according to the embodiment in which the side seam is essentially parallel with the direction of flow (bottom to top in the figure).

Skirt 21 comprises at least one side seam 43 where skirt 21 is joined upon itself (in a one-piece embodiment) or where two portions of material are joined to each other as part of the assembly of skirt 21 from separate components (three, in the preferred embodiment). In any case, side seam 43 extends downwardly from a point on the lower half of joint 27, preferably from a point in the apex region (i.e., the immediate vicinity of the apex) and most preferably (as illustrated), from the lower apex of joint 27. Side seam 43 extends downwardly towards the inflow portion of the prosthesis until it reaches the lower (or inflow) edge of skirt 21 located within the region indicated by I. Turning to FIG. 2, it may be seen that skirt 21 is attached to the frame such that the side seam 43 extends only the relatively short distance represented by a single cell of the frame. One advantage of such an embodiment is the reduction in the amount of any biological response to the seams, e.g., coagulation triggered by stitches or tissue folds.

Figure 3:
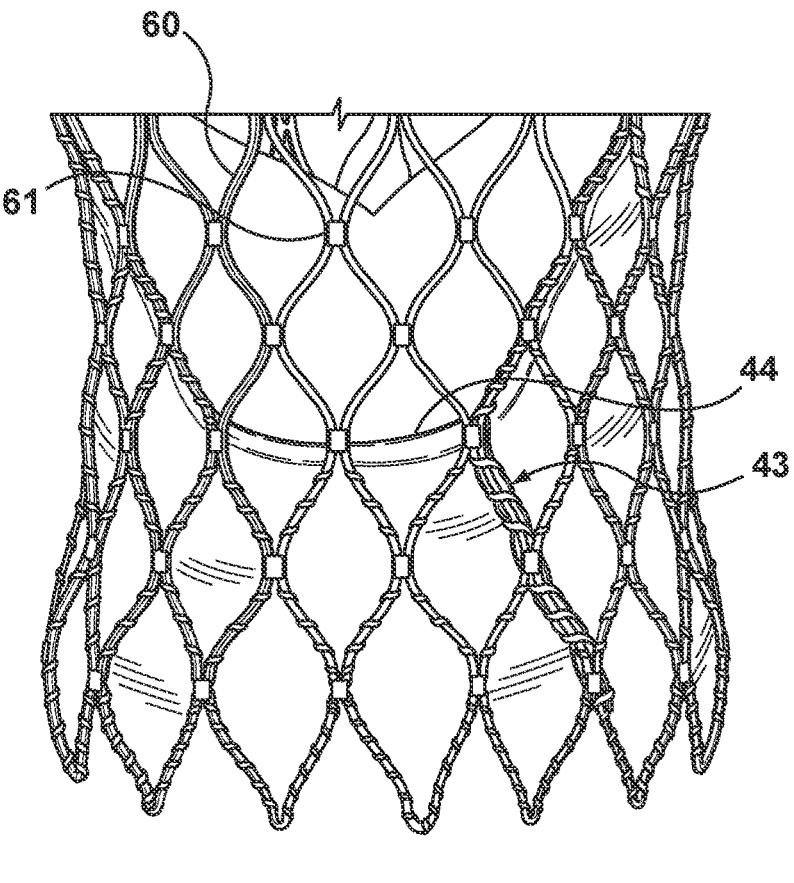
FIG. 3 is a close-up side view of the inflow end of a fully assembled valve body, including the surrounding frame, according to an alternative embodiment in which the side seam is angled with respect to the direction of flow (again, bottom to top in the figure).
Figure 4:
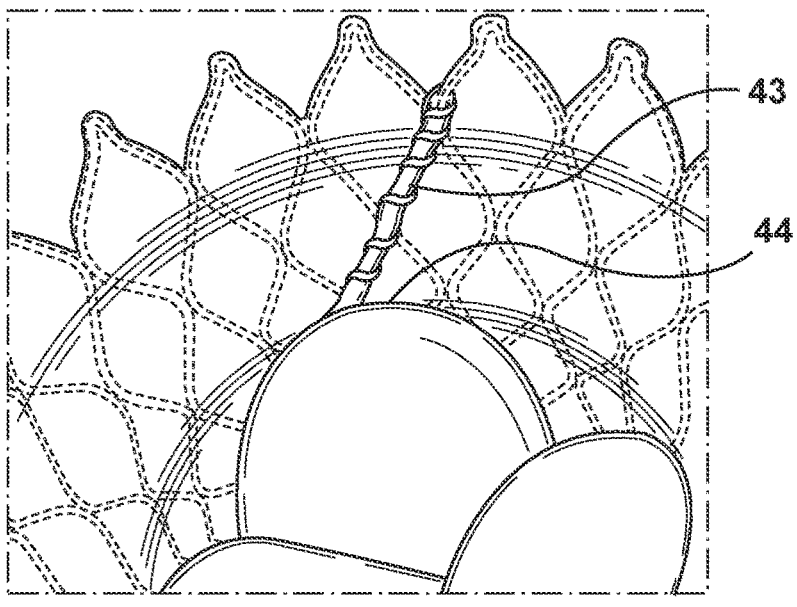
FIG. 4 is a close-up inverted perspective view of the interior of the embodiment of FIG. 3.

FIGS. 3 and 4 illustrate an alternative embodiment in which side seam 43 is angled with respect to the vertical (i.e., the longitudinal axis lying along the direction of flow through the valve 10). In this embodiment, the side seam 43 is somewhat longer than in the embodiment of FIG. 2, because side seam 43 lies generally aligned with the diagonal struts 60 extending between three consecutive nodes 61 of the frame, as opposed to spanning the open portion of a cell. Nonetheless, side seam 43 is still significantly shorter than it would be if it extended to a point on the upper half of joint 27 (e.g., locations where individual joints 27 come together). This embodiment has the advantage of orienting the side seam 43 behind the frame (compare FIGS. 3 and 4) to avoid a "pillow" effect, i.e., a tendency for side seam 43 to bulge outwardly from the interior of the frame.

Figure 5:
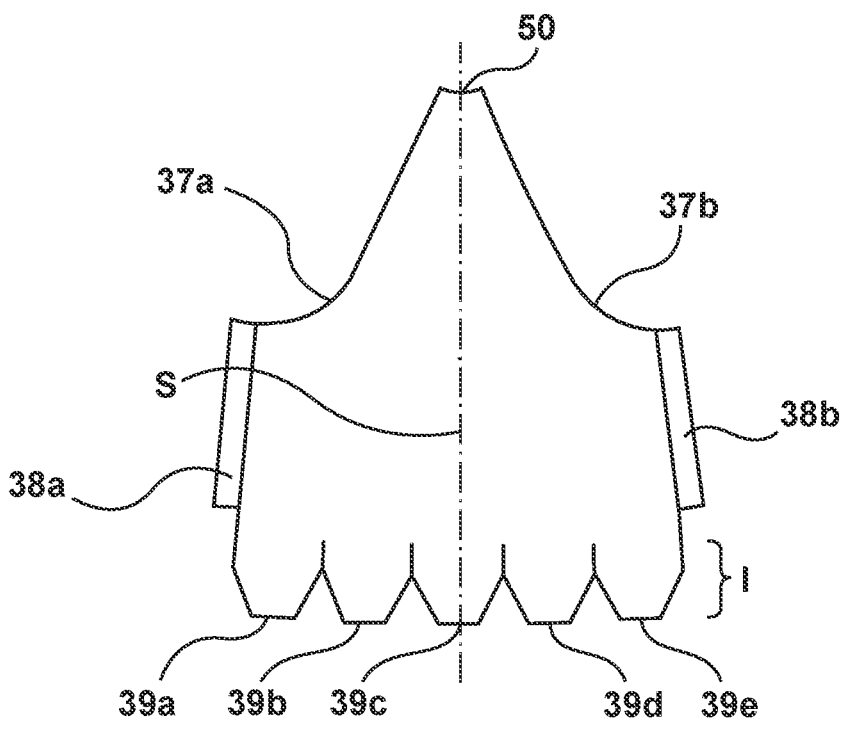
FIG. 5 is a schematic plan view of a portion of the valve skirt according to the embodiment of FIGS. 1 and 2.
Figure 6:
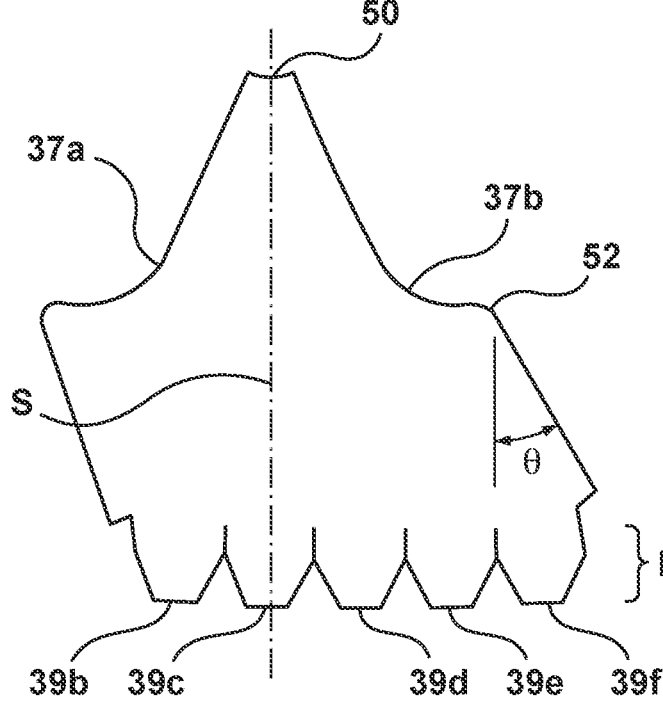
FIG. 6 is a schematic plan view of a portion of the valve skirt according to the embodiment of FIGS. 3 and 4.
Figure 7:
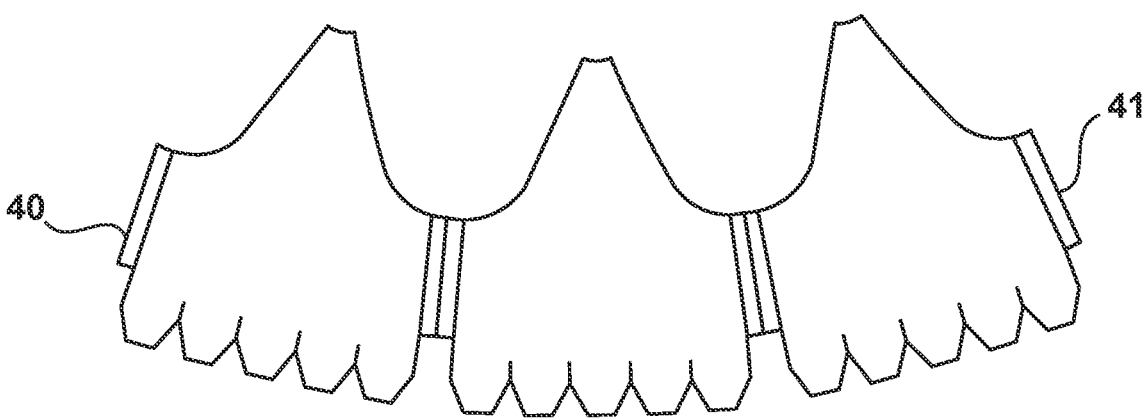
FIG. 7 is a partially assembled valve skirt according to the embodiment of FIG. 5.
Figure 8:
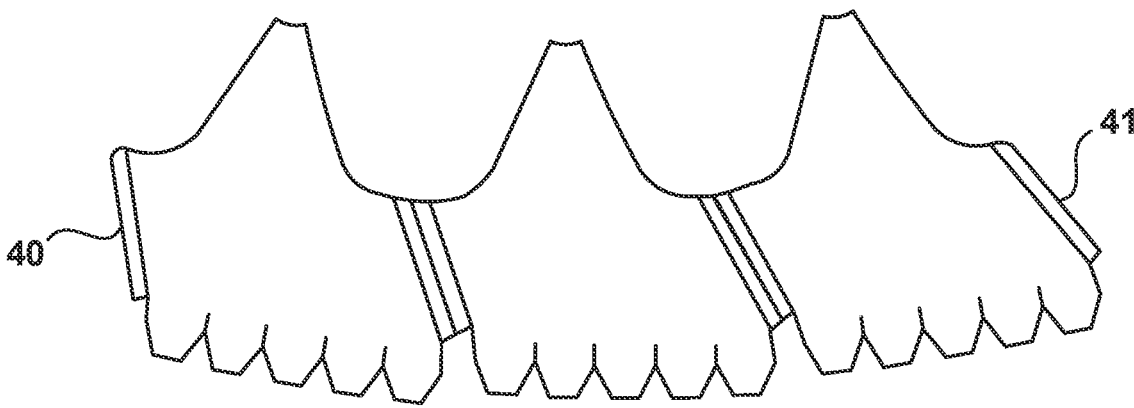
FIG. 8 is a partially assembled valve skirt according to the embodiment of FIG. 6.

FIGS. 5 and 6 schematically illustrate various geometrical features of a portion of skirt 21 corresponding to the embodiments of FIGS. 2 and 3-4, respectively. FIGS. 7 and 8 illustrate the assembly of the portions of FIGS. 5 and 6, respectively.

Skirt 21 preferably is constructed from the same material as leaflets 22, and includes scalloped areas 37*a-b*, reinforcing tabs 38*a-b* and multiple end tabs 39. Each scalloped area 37*a-b* is shaped to be joined to each other and then joined to a body 33 of a respective leaflet 22, as described illustrated earlier (see FIG. 1). Reinforcing tabs 38*a-b* include fold lines (not shown in FIG. 6 for clarity), except for reinforcing tabs 40 and 41 at the lateral ends of the skirt, which have only one fold apiece (see FIGS. 7-8). As described below, reinforcing tabs 40 and 41 are joined to one another, e.g., by sutures or gluing, so that skirt 21 forms a frustum of a cone. End tabs 39 are folded over the ends of the proximal-most row of cells of the frame to secure skirt 21 to the frame and seal against paravalvular bypass flows.

A line of symmetry S passes through a location substantially centered on the upper apex 50, and is substantially parallel to the longitudinal direction of flow. Notably, in the embodiment of FIG. 5, S symmetrically divides tabs 39*a-e* but does not symmetrically divide such tabs 39*b-f* in the embodiment of FIG. 6. This is due to the notable difference between the embodiments, i.e., the acute angle 8 that side seam 43 makes from the direction of flow in FIG. 6, which enables side seam 43 (in that embodiment) to follow the frame as described above. Note that side seam 43 still originates in the lower apex region, specifically at lower apex 52 (the vertex of the acute angle). It may also be said that the side seam 43 extends between the lower apex 52 and an end tab which does not lie on the axis S, i.e., end tab 39*b* or 39*f*, as opposed to end tab 39*c* which does lie on that axis.

Figure 9:
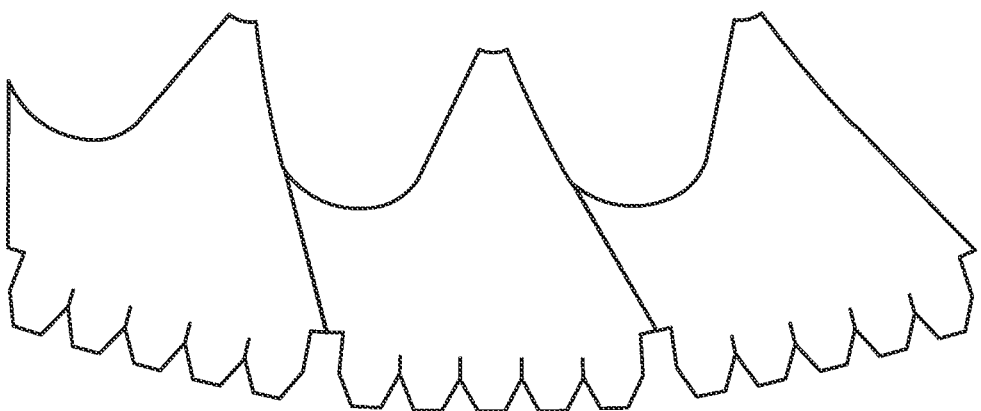
FIGS. 9 and 10 are partially assembled valve skirts according to other embodiments.
Figure 10:
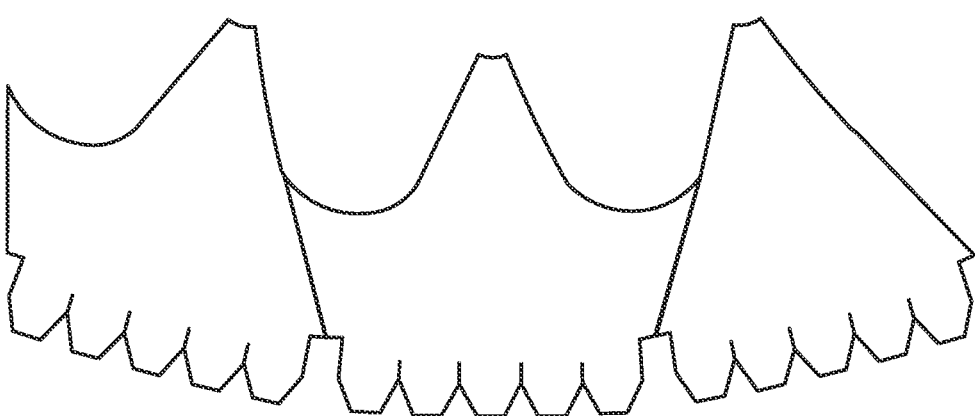

FIGS. 9 and 10 schematically illustrate less preferred embodiments; for the sake of clarity, some details common to the preferred embodiments above are omitted. In these two embodiments, the angled seams originate at higher locations on the joints other than the lower apex but still in the lower half of the seams. As FIG. 10 shows in particular, the portions of such embodiments do not necessarily have identical shapes. The embodiments of FIGS. 9 and 10 are less preferred than other embodiments because of their relatively complicated configuration as compared to the preferred embodiments discussed above, and also because the side seams in these embodiments are generally not be a short as those in the preferred embodiments.

In general, assembly of valve body 14 from skirt 21 and leaflets 22 is performed as described in U.S. Pat. No. 7,914,569 as modified to accommodate the modifications described here. Adjoining leaflets 22 then are fastened together along adjacent seams, resulting in a leaflet assembly.

Referring again to FIG. 1, valve body 14 is shown as it would appear when affixed to the frame, but with the frame omitted to better illustrate where the valve body is affixed to the frame. During the step of affixing the valve body to the frame, flaps 36 of adjacent leaflets are affixed, e.g., by sutures, to span a cell of the frame to support commissures 24 and end tabs 39 are folded over and affixed to the most proximal row of cells of the frame, i.e., at the inflow end to the prosthesis.

Valve body 14 also is attached to the frame along seams 43 formed by the reinforcing tabs. Each joint 44 is aligned with and fastened to (e.g., by sutures or glue) to a curved contour defined by the struts and nodes that form the cells of the frame, so that joint 44 is affixed to and supported by the frame over most of the length of the joint. As discussed above, the configuration of the cells in the frame may be specifically customized to define a curved contour that supports joints 44 of the valve body.

When completely assembled to the frame, valve body 14 is affixed to the frame along the edges of flaps 36 of the commissures, end tabs 39, leaflet seams 42, reinforcing tab seams 43 and joints 44. In this manner, forces imposed on leaflets 22, commissures 24 and joints 44 are efficiently and evenly distributed over the valve body and transferred to the frame, thus reducing stress concentration and fatigue of the valve body components.

Implantation of the valve prosthesis is performed in a conventional manner.

While the description above uses preferred embodiments to describe certain details, the broadest scope of the disclosure includes other embodiments, as well as methods of carrying out the same principles that do not depend upon the specific physical components mentioned above but nonetheless achieve the same or equivalent results. Therefore, the full scope of the invention is described by the following claims.

What is claimed is:

1. A valve body for use in a prosthetic heart valve, the valve body comprising:

a skirt having a lower edge;

a plurality of valve leaflets, at least one valve leaflet being joined to the skirt to form a leaflet-to-skirt joint, the leaflet-to-skirt joint having an upper portion and a lower portion, the upper portion having an uppermost point;

the skirt further having a side seam extending from a first terminal end at the leaflet-to-skirt joint toward the lower edge of the of the skirt to a second terminal end, the first terminal end and the second terminal end defining a skirt side seam length that is shorter than a line extending from the second terminal end to the uppermost point on the upper portion of the leaflet-to-skirt joint in a longitudinal direction.

2. The valve body of claim 1, wherein leaflet-to-skirt joint has an upper half and a lower half, the skirt side seam extending from the lower half.

3. The valve body of claim 2, wherein the skirt side seam extends downwardly in a longitudinal direction from the lower half of the leaflet-to-skirt joint toward the lower edge of the skirt.

4. The valve body of claim 2, wherein the skirt side seam extends downwardly in a longitudinal direction from the lower half of the leaflet-to-skirt joint to the lower edge of the skirt.

5. The valve body of claim 1, wherein the skirt side seam extends downwardly in a longitudinal direction from the lower portion of the leaflet-to-skirt joint toward the lower edge of the skirt.

6. The valve body of claim 1, wherein the skirt side seam extends downwardly in a longitudinal direction from the lower portion of the leaflet-to-skirt joint to the lower edge of the skirt.

7. The valve body of claim 1, wherein the valve leaflets have free edges forming coaptation edges arranged to meet in an area of coaptation.

8. The valve body of claim 1, wherein the leaflet-to-skirt joint lower portion has a lower apex, the skirt side seam extending from the leaflet-to-skirt joint in the immediate vicinity of the lower apex.

9. The valve body of claim 1, wherein the leaflet-to-skirt joint lower portion has a lower apex, the skirt side seam extending from the lower apex.

10. The valve body of claim 1 in combination with a frame having a plurality of cells, the valve body being supported by the frame.

11. The valve body of claim 1 in combination with a frame having a plurality of cells and a longitudinal axis, the valve body being supported by the frame and the skirt side seam being substantially parallel to the longitudinal axis.

12. The valve body of claim 1 in combination with a frame having a plurality of cells and a longitudinal axis, the valve body being supported by the frame and the skirt side seam making an acute angle with the longitudinal axis.

13. The valve body of claim 1 in combination with a frame having a longitudinal axis and a plurality of struts, the valve body being supported by the frame, and the skirt side seam being generally aligned with at least one of the struts.

14. The valve body of claim 1 in combination with a frame having a longitudinal axis and a plurality of struts, the valve body being supported by the frame, and the skirt side seam being generally aligned with a plurality of the struts and making an acute angle with the longitudinal axis of the frame.

15. The valve body of claim 1 in combination with a frame having a longitudinal axis and cells comprising struts and nodes, the valve body being supported by the frame, and the skirt side seam being generally aligned with at least one of the struts and making an acute angle with the longitudinal axis of the frame.

16. The valve body of claim 1 in combination with a frame having a longitudinal axis and cells comprising struts and nodes, the valve body being supported by the frame, and the skirt side seam being generally aligned with a plurality of the struts and making an acute angle with the longitudinal axis of the frame.

17. A valve body for use in a prosthetic heart valve, the valve body comprising:

a skirt having an inflow edge;

a plurality of valve leaflets where at least one of the valve leaflets is joined to the skirt to form a leaflet-to-skirt joint that includes an upper half and a lower half; and the skirt further having a seam that extends from a first terminal end at the lower half of the leaflet-to-skirt joint toward the inflow edge of the skirt.

18. The valve body of claim 17, wherein the leaflet-to-skirt joint lower half has a lower apex, the skirt seam extending from the leaflet-to-skirt joint in the immediate vicinity of the lower apex.

19. The valve body of claim 17, wherein the lower half includes a lower apex, the skirt seam extending from the lower apex.

20. The valve body of claim 17, wherein the skirt seam extends downwardly in a longitudinal direction from the lower half of the leaflet-to-skirt joint toward the inflow edge of the skirt.

21. The valve body of claim 17, wherein the skirt seam extends downwardly in a longitudinal direction from the lower half of the leaflet-to-skirt joint to the inflow edge of the skirt.

22. The valve body of claim 17, wherein the skirt seam extends from the lower half of the leaflet-to-skirt joint to the inflow edge of the skirt.

23. The valve body of claim 17, wherein the valve leaflets have lateral end regions, a plurality of the lateral end regions being attached to form commissures.

24. The valve body of claim 23, wherein the lower half of the leaflet-to-skirt joint is circumferentially offset from at least one of the commissures.

25. The valve body of claim 17, wherein the leaflet-to-skirt joint is curved.

26. The valve body of claim 17, wherein the valve leaflets have free edges forming coaptation edges arranged to meet in an area of coaptation.

27. The valve body of claim 17 in combination with a frame having a plurality of cells, the valve body being supported by the frame.

28. The valve body of claim 17 in combination with a frame having a plurality of cells and a longitudinal axis, the valve body being supported by the frame and the skirt seam being substantially parallel to the longitudinal axis.

29. The valve body of claim 17 in combination with a frame having a plurality of cells and a longitudinal axis, the valve body being supported by the frame and the skirt seam making an acute angle with the longitudinal axis.

30. The valve body of claim 17 in combination with a frame having a longitudinal axis and a plurality of struts, the valve body being supported by the frame, and the skirt seam being generally aligned with at least one of the struts.

31. The valve body of claim 17 in combination with a frame having a longitudinal axis and a plurality of struts, the valve body being supported by the frame, and the skirt seam being generally aligned with a plurality of the struts and making an acute angle with the longitudinal axis of the frame.

32. The valve body of claim 17 in combination with a frame having a longitudinal axis and cells comprising struts and nodes, the valve body being supported by the frame, and the skirt seam being generally aligned with at least one of the struts and making an acute angle with the longitudinal axis of the frame.

33. The valve body of claim 17 in combination with a frame having a longitudinal axis and cells comprising struts and nodes, the valve body being supported by the frame, and the skirt seam being generally aligned with a plurality of the struts and making an acute angle with the longitudinal axis of the frame.

* * * * *